United States Patent [19]

Hewell, III

[11] Patent Number: 5,269,781
[45] Date of Patent: Dec. 14, 1993

[54] SUCTION-ASSISTED ELECTROCAUTERY UNIT

[76] Inventor: Todd S. Hewell, III, 4 Stonewood Dr., St. Charles, Ill. 60174

[21] Appl. No.: 896,167

[22] Filed: Jun. 10, 1992

[51] Int. Cl.⁵ .............................................. A61B 17/39
[52] U.S. Cl. ...................................... 606/45; 604/35; 606/29; 606/49
[58] Field of Search ...................... 606/39, 40, 41, 42, 606/45, 49, 50, 32, 29

[56] References Cited

U.S. PATENT DOCUMENTS

| | | | |
|---|---|---|---|
| 4,562,838 | 1/1986 | Walker | 606/45 |
| 4,719,914 | 1/1988 | Johnson | 606/49 X |
| 4,744,360 | 5/1988 | Bath | 604/35 X |
| 4,919,129 | 4/1990 | Weber, Jr. et al. | 606/45 X |
| 4,960,419 | 10/1990 | Rosenberg | 606/45 |
| 5,061,268 | 10/1991 | Fleenor | 606/45 |
| 5,071,418 | 12/1991 | Rosenbaum | 604/35 X |
| 5,085,657 | 2/1992 | Ben-Simhon | 606/45 X |
| 5,088,997 | 2/1992 | Delahuerga et al. | 606/45 X |

Primary Examiner—Peter A. Aschenbrenner
Attorney, Agent, or Firm—Wood, Phillips, VanSanten, Hoffman & Ertel

[57] ABSTRACT

Smoke emitted during an electrocautery procedure may be removed from the environment of the procedure through the use of an electrocautery knife having an elongated handle provided with an inlet port at the end of the handle mounting the knife blade, an outlet port at the opposite end of the handle and adapted to be connected to available suction or vacuum, and an internal passage extending between the ports.

3 Claims, 1 Drawing Sheet

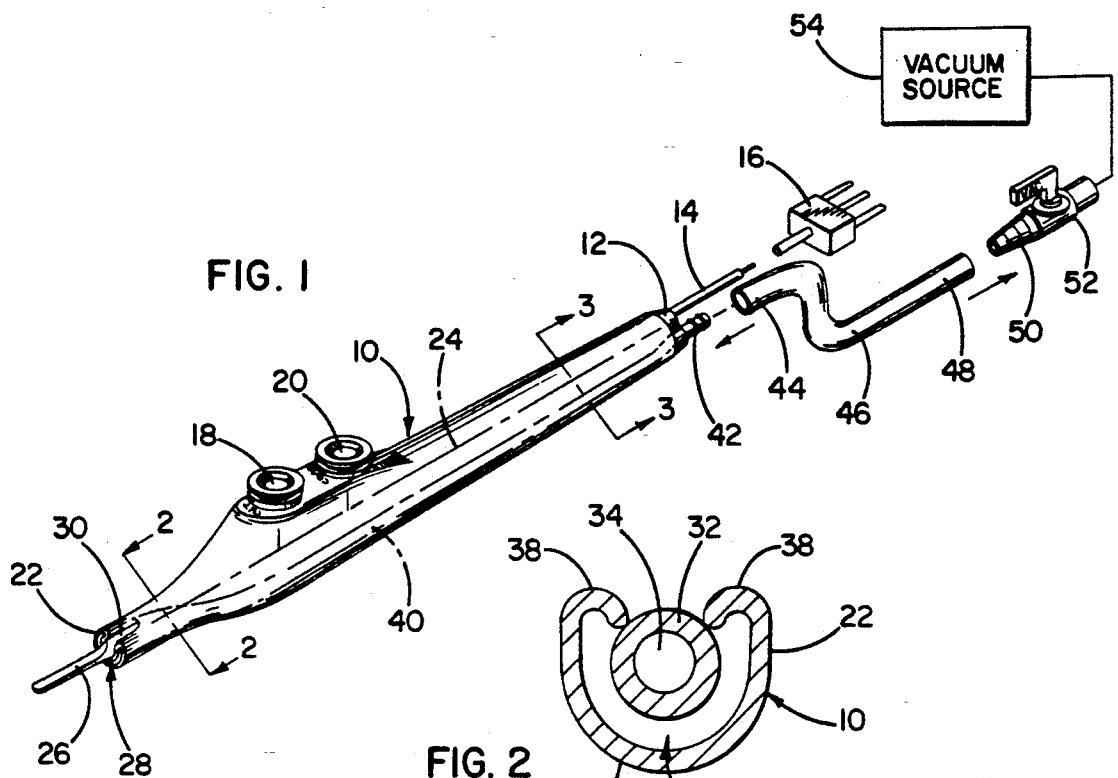
FIG. 1
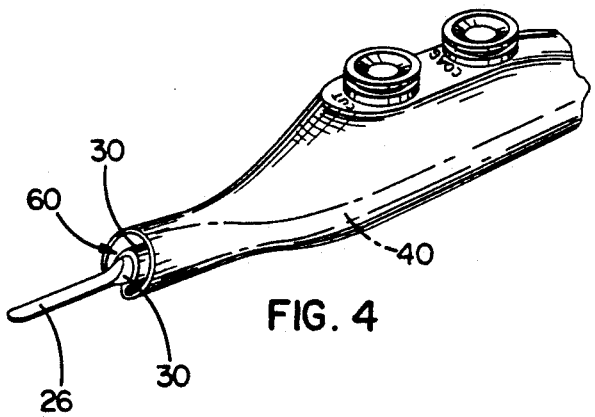
FIG. 2
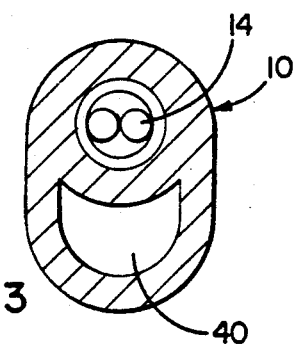
FIG. 3
FIG. 4
FIG. 5
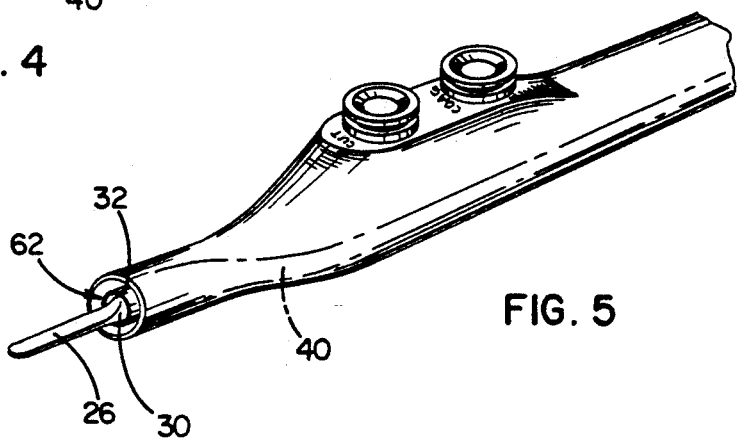

SUCTION-ASSISTED ELECTROCAUTERY UNIT

FIELD OF THE INVENTION

This invention relates to medical instruments, and more particularly, to an electrocautery knife.

BACKGROUND OF THE INVENTION

Electrocautery knives are extensively employed in surgeries of widely varying types. As is well known, they are utilized to both dissect tissue and to cauterize blood vessels. In either case, the tissue or blood vessel being contacted by the electrocautery knife is subject to the elevated temperatures produced by the knife and, in turn, has its temperature elevated to the point where thermal decomposition occurs.

Products of the thermal decomposition are visible as smoke and generally apparent by reason of having an offensive odor as well. In either case, the decomposition products are likely to be an irritant to healthcare workers in the vicinity of the surgery being performed.

Moreover, little is known about the composition of the smoke particles but a recent study published in the May, 1992 issue of "Plastic and Reconstructive Surgery" entitled *The Mutagenicity of Electrocautery Smoke* has concluded that the smoke produced with an electrocautery knife during reduction mammaplasty was found to be mutagenic to at least one strain of salmonella. Thus, while it is not known whether the smoke produced during use of an electrocautery knife represents a serious health hazard, the fact that such smokes were able to alter the genetic makeup of certain salmonella bacteria suggests the presence of a potential health risk requiring that healthcare workers, particularly surgeons, working in the vicinity of a surgery employing an electrocautery knife should attempt to limit their exposure to the smoke produced by the knife.

The present invention is directed overcoming the above problem.

SUMMARY OF THE INVENTION

It is the principal object of the invention to provide a new and improved electrocautery knife. More specifically, it is an object of the invention to provide an electrocautery knife that prevents smoke generated during an electrocautery procedure from entering the environment in which the procedure is being performed.

An exemplary embodiment of the invention achieves the foregoing object in an electrocautery knife construction which includes an elongated handle having opposite ends. A metallic blade is mounted at one of the ends and an electrical connector is located at or near the other of the ends. Control means are mounted in the handle and operatively associated with the blade and the electrical connector to control the heating of the blade during the performance of an electrocautery procedure. The structure further includes an inlet port in the handle in proximity to the blade and adjacent the end whereat the blade is mounted. An outlet port is provided in the handle at or near the other end of the handle and a passage is located within the handle to interconnect the two ports.

As a consequence of the foregoing, the outlet may be connected to a vacuum or so called "suction" source typically found in healthcare environments so that smoke generated at the blade during an electrocautery procedure will be drawn into the inlet and through the passage to the vacuum source. Thus, the smoke is withdrawn from the environment almost as soon as it is generated by reason of the proximity of the inlet port to the blade.

A preferred embodiment of the invention contemplates that the inlet port extend at least partially about the blade.

In one embodiment, the inlet port is under the blade while in another embodiment, the inlet port is above the blade. In either of the two embodiments, the inlet port is generally U-shaped about the blade.

In still another embodiment, the inlet port extends peripherally around the blade. In this embodiment, the port is generally circular as well as generally concentric with the blade and a mounting means for the blade.

Other objects and advantages will become apparent from the following specification taken into connection with the accompanying drawings.

DESCRIPTION OF THE DRAWINGS

FIG. 1 is a perspective view of one embodiment of an electrocautery knife made according to the invention;

FIG. 2 is a sectional view taken approximately along the line 2—2 of FIG. 1;

FIG. 3 is a sectional view taken approximately along the line 3—3 of FIG. 1;

FIG. 4 is a partial perspective view of a modified embodiment of the invention;

FIG. 5 is a view similar to FIG. 4 but of still another modified embodiment of the invention.

DESCRIPTION OF THE PREFERRED EMBODIMENTS

An examplary embodiment of an electrocautery knife made according to the invention is illustrated in FIGS. 1-3 inclusive. As illustrated, the invention contemplates a disposable knife including a handle, generally designated 10. However, it is to understood that the principles of the invention are equally applicable non-disposable knives.

The handle 10 will typically be formed of a plastic material that is substantially heat resistant. As is conventional, the handle 10 is elongated and has one end 12 at which an electrical cord 14 ultimately connected to a plug 16 enters the handle 10. The cord 14 extends within the handle 10 to conventional electrical control buttons 18 and 20 located on the top of the handle 10 intermediate the end 12 and the opposite end 22 of the handle 10. A conventional connection shown schematically at 24 connects the cord 14 to the control buttons 18 and 20 and also to a metallic, electrocautery blade 26 which extends from the end 22. Suitable operation of the control buttons 18 and 20 conventionally control the temperature level of the blade 26 as desired.

As noted, the interrelationship between the cord 14, plug 16, control buttons 18 and 20, and the blade 26 along with the interconnection 24 are conventional. They may, for example, follow the construction found in a commercial, disposable electrocautery knife manufactured by Cameron-Miller as its model 16-1509.

As seen in FIG. 1, the end 22 of the handle 10 is equipped with an inlet port generally designated 28. The port is U-shaped and disposed about the base 30 of the blade 26. In the embodiment illustrated in FIG. 1, the U-shaped port 28 is in the upright orientation of a U so as to be located generally under the blade 26. As seen in FIG. 2, the end 22 includes an interior, elongated, sleeve-like element 32 having a central opening 34. The element 32 serves as a mounting means for receiving the base 30 of the blade 26. Preferably, the sleeve-like element 32 is integrally molded with the remainder of the handle 10.

Part of the sleeve-like element 32 defines the inner-boundary of the U-shaped port 28 while another section 36 of the handle 10 near the end 22 is spaced radially outwardly from the sleeve-like element 32 so as to be generally concentric with the opening 32 but spaced therefrom on the lower side thereof. Generally radially directed segments 38 of the handle surface extend inwardly and merge with the sleeve-like element 32 to define opposite ends of the port 28.

Returning to FIG. 1, an elongated passage, generally designated 40, is in fluid communication with the inlet port 28 and is located entirely within the handle 10. It extends from the inlet port 28 at the end of 22 to the end 12 whereat it terminates in a rearwardly projecting male hose connector 42. As illustrated in FIG. 1, the hose connector 42 extends from the end 12 but generally speaking, it is only necessary that the hose connector 42 be located somewhere near the end 12 so as not to interfere with the grip of a user on the handle 10 at a location whereat the control buttons 18 and 20 may be conveniently manipulated.

The male hose connector 42 defines an outlet port which may be connected to one end 44 of a piece of surgical tubing 46. The opposite end 48 of the tubing 46 may be placed upon the inlet port 50 of a conventional vacuum valve 52 which in turn is connected to a conventional vacuum source 54 as is typically found in healthcare centers or hospitals and perhaps more conventionally referred to as a "suction line".

As a consequence of the foregoing, when the knife is connected to the vacuum source 54 and then placed in use, smoke caused by contact of the blade 26 with tissue will all be generated immediately adjacent the end 22 of the handle 10. This is, of course, the same location at which the inlet port 28 is placed and when the same is in fluid communication with the vacuum source 54 via the passage 40, the resulting low pressure at the port 28 will result in the smoke being generated entering the port 28 to be withdrawn ultimately to the vacuum source 54. Of course, suitable filtering systems may be associated with the vacuum source 54 and designed to dispose of contaminants in the material being drawn to the vacuum source 54.

As seen in FIG. 3, the passage 40 may be generally crescent shaped along the vast majority of its length within the handle 10. In this way, the passage 40 will not disturb the conventional orientation of the electrical components of the knife.

In some instances, it may be desirable that the inlet port be located basically above the blade 26. In this instance, the embodiment illustrated in FIG. 4 may be used. Here, an inverted U-shaped inlet port 60 is also partially concentric with the blade 26 but is disposed above the base 30 thereof rather than below the base as illustrated in FIG. 1. In actuality, the port 60 may simply be regarded as a 180 degree inversion of the port 28.

Still another embodiment is illustrated in FIG. 5. In this embodiment, a peripheral port, generally designated 62, is employed. That is to say, the port 62 has an arcuate extent of 360° and is generally concentric with the mounting sleeve 32 for the base 30 of the blade 26.

From the foregoing, it will be appreciated that an electrocautery knife made according to the invention provides a means whereby smoke generated during an electrocauterization procedure may be evacuated from the area of the cut or coagulation as soon as the smoke is generated. It is to be particularly noted that no effort is made to modulate vacuum during the procedure, although if greater complexity could be tolerated, those skilled in the art will readily appreciate that control over the presence of vacuum at ports 28, 60 or 62 could be exercised in response to operation of the control buttons of 18 and 20 through any of a variety of means, including a remote, solenoid controlled valve or the like.

The use of a passage 40 that is actually located within the handle 10 itself is highly advantageous since the handle may then be conveniently designed for easy manipulation by the user and the presence of the vacuum passage will not interfere with that ease of use or the comfort of the user. Furthermore, the use of a breakable connection to the vacuum source at the end 12 allows the electrocautery knife of the present invention to be used in a conventional fashion if desired. That is to say, if a particular user does not wish to employ suction for smoke removal purposes, the user merely need not connect a tube such as the tubing 46 to the hose connector 42.

I claim:

1. An electrocautery knife comprising:
   an elongated handle having opposite ends;
   a metallic blade mounted at one of said ends;
   an electrical conductor at or near the other of said ends;
   control means mounted in said handle and operatively associated with said blade and said electrical conductor for controlling the heating of said blade;
   an inlet port in said handle in proximity to said blade adjacent said one end, said inlet port being generally U-shaped about said blade;
   an outlet port in said handle at or near said other end; and
   a passage within said handle interconnecting said ports;
   whereby said outlet may be connected to a vacuum source so that smoke generated at said blade during an electrocautery procedure will be drawn into said U-shaped inlet through said passage to the vacuum source.

2. An electrocautery knife comprising:
   an elongated handle having opposite ends;
   a metallic blade mounted at one of said ends;
   an electrical conductor at or near the other of said ends;
   control means mounted in said handle and operatively associated with said blade and said electrical conductor for controlling the heating of said blade;
   an inlet port in said handle in proximity to said blade adjacent said one end, said inlet port being generally U-shaped about said blade and located under said blade;
   an outlet port in said handle at or near said other end; and a passage within said handle interconnecting said ports;
   whereby said outlet may be connected to a vacuum source so that smoke generated at said blade during an electrocautery procedure will be drawn into said U-shaped inlet through said passage to the vacuum source.

3. An electrocautery knife comprising:
   an elongated handle having opposite ends;
   a metallic blade mounted at one of said ends;

an electrical conductor at or near the other of said ends;

control means mounted in said handle and operatively associated with said blade and said electrical conductor for controlling the heating of said blade;

an inlet port in said handle in proximity to said blade adjacent said one end, said inlet port having a generally inverted, U-shaped configuration about said blade;

an outlet port in said handle at or near said other end; and a passage within said handle interconnecting said ports;

whereby said outlet may be connected to a vacuum source so that smoke generated at said blade during an electrocautery procedure will be drawn into said U-shaped inlet through said passage to the vacuum source.

* * * * *